United States Patent
Liu et al.

(10) Patent No.: US 12,275,876 B2
(45) Date of Patent: Apr. 15, 2025

(54) HOT MELT PROCESSABLE (METH)ACRYLATE-BASED MEDICAL ADHESIVES

(71) Applicant: Solventum Intellectual Properties Company, Maplewood, MN (US)

(72) Inventors: Jungkang Liu, St. Paul, MN (US); Athanasios Touris, Santa Ana, CA (US); Shijing Cheng, Woodbury, MN (US); Wengsheng Xia, Woodbury, MN (US); Ying Zhang, Woodbury, MN (US)

(73) Assignee: Solventum Intellectual Properties Company, Maplewood, MN (US)

( * ) Notice: Subject to any disclaimer, the term of this patent is extended or adjusted under 35 U.S.C. 154(b) by 827 days.

(21) Appl. No.: 17/417,169

(22) PCT Filed: Dec. 23, 2019

(86) PCT No.: PCT/IB2019/061291
§ 371 (c)(1),
(2) Date: Jun. 22, 2021

(87) PCT Pub. No.: WO2020/136555
PCT Pub. Date: Jul. 2, 2020

(65) Prior Publication Data
US 2022/0081593 A1    Mar. 17, 2022

Related U.S. Application Data

(60) Provisional application No. 62/785,319, filed on Dec. 27, 2018.

(51) Int. Cl.
C09J 7/38      (2018.01)
A61L 26/00    (2006.01)
C09J 7/35      (2018.01)

(52) U.S. Cl.
CPC .......... *C09J 7/385* (2018.01); *A61L 26/0014* (2013.01); *A61L 26/0061* (2013.01); *C09J 7/35* (2018.01); *C09J 2301/416* (2020.08); *C09J 2401/006* (2013.01); *C09J 2433/00* (2013.01); *C09J 2475/006* (2013.01)

(58) Field of Classification Search
None
See application file for complete search history.

(56) References Cited

U.S. PATENT DOCUMENTS

| | | |
|---|---|---|
| 3,645,835 A | 2/1972 | Hodgson |
| 4,595,001 A | 6/1986 | Potter |
| 4,737,559 A | 4/1988 | Kellen |
| 4,838,253 A | 6/1989 | Brassington |
| 5,088,483 A | 2/1992 | Heinecke |
| 5,147,698 A | 9/1992 | Cole |
| 5,160,315 A | 11/1992 | Heinecke |
| 5,194,550 A | 3/1993 | Rance |
| 5,804,610 A | 9/1998 | Hamer |
| 5,886,122 A | 3/1999 | Oka |
| 5,891,076 A | 4/1999 | Fabo |
| 6,051,747 A | 4/2000 | Lindqvist |
| 6,294,249 B1 | 9/2001 | Hamer |
| 6,558,790 B1 | 5/2003 | Holguin |
| 7,056,413 B2 | 6/2006 | Caspari |
| 7,115,682 B2 | 10/2006 | Guo |
| 7,608,656 B2 | 10/2009 | Saitama |
| 7,851,568 B2 | 12/2010 | Imai |
| 8,153,742 B2 | 4/2012 | Luciano |
| 8,263,680 B2 | 9/2012 | Luciano |
| 8,663,811 B2 | 3/2014 | Everaerts |
| 9,701,873 B2 * | 7/2017 | D'Haese ................ C09J 133/02 |
| 2010/0331785 A1 | 12/2010 | Fabo |
| 2011/0212325 A1 | 9/2011 | Determan |
| 2017/0096588 A1 | 4/2017 | Demoulin |
| 2018/0340098 A1 | 11/2018 | Tanabe |

FOREIGN PATENT DOCUMENTS

| | | |
|---|---|---|
| CN | 1222179 | 7/1999 |
| CN | 107922811 | 4/2018 |
| EP | 0501124 | 9/1992 |
| EP | 0608891 | 8/1994 |
| EP | 2920264 | 9/2015 |
| JP | 4849200 | 1/2012 |
| WO | 2013-048735 | 4/2013 |
| WO | 2015-134249 | 9/2015 |
| WO | 2016-167924 | 10/2016 |
| WO | 2018-017560 | 1/2018 |

OTHER PUBLICATIONS

International Search Report for PCT International Application No. PCT/IB2019/061291, mailed on Dec. 10, 2019, 5 pages.

* cited by examiner

*Primary Examiner* — Sanza L. McClendon

(57) ABSTRACT

Adhesive articles include a substrate; and a hot melt processable pressure sensitive adhesive on the substrate. The hot melt processable pressure sensitive adhesive is a (meth) acrylate-based copolymer that is the reaction product of a reaction mixture that is free of acidic or basic monomers, and includes an alkyl (meth)acrylate, a hydroxyl-functional (meth)acrylate, and a photocrosslinker. The (meth)acrylate-based polymer is prepared in a thermoplastic package.

20 Claims, No Drawings

HOT MELT PROCESSABLE (METH)ACRYLATE-BASED MEDICAL ADHESIVES

FIELD OF THE DISCLOSURE

This disclosure relates to (meth)acrylate-based pressure sensitive adhesives that may be used to form adhesive articles, such as tapes and other medical articles useful in medical applications.

BACKGROUND

A wide range of adhesive articles are used in medical applications. These adhesive articles include gels used to attach electrodes and other sensing devices to the skin of a patient, a wide range of tapes to secure medical devices to a patient, and adhesive dressings used to cover and protect wounds.

Many of the adhesive articles use pressure sensitive adhesives. Pressure sensitive adhesives are well known to one of ordinary skill in the art to possess certain properties at room temperature including the following: (1) aggressive and permanent tack, (2) adherence with no more than finger pressure, (3) sufficient ability to hold onto an adherend, and (4) sufficient cohesive strength to be removed cleanly from the adherend. Materials that have been found to function well as pressure sensitive adhesives are polymers designed and formulated to exhibit the requisite viscoelastic properties resulting in a desired balance of tack, peel adhesion, and shear strength. The most commonly used polymers for preparation of pressure sensitive adhesives are natural rubber, synthetic rubbers (e.g., styrene/butadiene copolymers (SBR) and styrene/isoprene/styrene (SIS) block copolymers), various (meth)acrylate (e.g., acrylate and methacrylate) copolymers, and silicones.

One problem with using adhesive articles for medical applications is that the removal of adhesive article can cause trauma to the skin. This is particularly troublesome in patients with sensitive skin, such as infants and the elderly, and can become severe with chronic patients where adhesive articles are repeatedly attached and removed over a long term period.

Various attempts have been made to mitigate this problem with adhesive articles. In particular, health care professionals utilize removal techniques to mitigate skin trauma. One way to mitigate trauma to the skin is to remove the adhesive article using a slow peel at a high angle to avoid stretching the skin. Another way to mitigate trauma, when the adhesive article is stretchable, is to pull straight out (as close to a 0° angle as possible) to induce stretch releasing of the adhesive layer from the skin. Also, manufactures of adhesive articles have developed articles that mitigate skin trauma by reducing adhesion to skin. So called "gentle-to-skin adhesives" have been developed that do not strip off skin cells or cause pain significantly when removed.

A variety of gentle-to-skin articles and dressings that use gentle-to-skin adhesives have been described. A gentle-to-skin adhesive is described in US Patent Publication No. 2011/0212325 (Determan et al.) which describes an electron beam and gamma radiation crosslinked silicone gel adhesive that may use either nonfunctional or functional poly diorganosiloxanes. In U.S. Pat. No. 4,838,253 (Brassington, et al.), a silicone gel coated dressing is described. In U.S. Pat. No. 6,051,747 (Lindqvist, et al.), a foam absorbent dressing is described wherein the foam dressing is coated with a layer of hydrophobic gel. Also, U.S. Pat. No. 5,891,076 (Fabo) describes a hypertrophic scar dressing that includes silicone-gel on that side of the dressing which lies against the user's skin and a flexible carrier sheet embodied within the silicone-gel such that the gel forms continuous layers on both sides of the carrier, and US Patent Publication No. 2010/0331785 (Fabo et al.) describes a dressing that includes a liquid impermeable film layer coated with a skin friendly adhesive on the side intended to adhere to the skin.

SUMMARY

This disclosure relates to adhesive articles with hot melt processable (meth)acrylate-based pressure sensitive adhesives, hot melt processable packaged (meth)acrylate-based pressure sensitive adhesives, and methods of making adhesive articles.

Disclosed herein are adhesive articles. In some embodiments, the article comprises a substrate; and a hot melt processable pressure sensitive adhesive disposed on at least a portion of the substrate. The hot melt processable pressure sensitive adhesive comprises a (meth)acrylate-based copolymer that is the reaction product of a reaction mixture that is substantially free of acidic or basic monomers. The reaction mixture comprises, as the polymerizable components, 70-96 parts by weight of a first (meth)acrylate monomer of general Formula I:

$$CH_2=CR^1-(CO)-OR^2 \quad \text{Formula I}$$

where $R^1$ is hydrogen or a methyl group, and $R^2$ is an alkyl, heteroalkyl, alkenyl, or aryl group, and 4-30 parts by weight of a second (meth)acrylate monomer of general Formula II:

$$CH_2=CR^1-(CO)-OR^3 \quad \text{Formula II}$$

where $R^1$ is hydrogen or a methyl group, and $R^3$ is a hydroxyl substituted alkyl group, a hydroxyl substituted heterocyclic group, a hydroxyl substituted aryl group, or a hydroxyl substituted macromolecule, and a co-polymerizable photocrosslinker.

Also disclosed are hot melt processable packaged adhesive compositions. In some embodiments, the packaged adhesive composition comprises a hot melt processable adhesive comprising a polymerized (meth)acrylate-based copolymer formed from a polymerizable pre-adhesive mixture, and a packaging material. The polymerizable pre-adhesive mixture composition is substantially free of acidic or basic monomers and comprises 70-96 parts by weight of a first (meth)acrylate monomer of general Formula I:

$$CH_2=CR^1-(CO)-OR^2 \quad \text{Formula I}$$

wherein $R^1$ is hydrogen or a methyl group, and $R^2$ is an alkyl, heteroalkyl, alkenyl, or aryl group, and 4-30 parts by weight of a second (meth)acrylate monomer of general Formula II:

$$CH_2=CR^1-(CO)-OR^3 \quad \text{Formula II}$$

where $R^1$ is hydrogen or a methyl group, and $R^3$ is a hydroxyl substituted alkyl group, a hydroxyl substituted heterocyclic group, a hydroxyl substituted aryl group, or a hydroxyl substituted macromolecule, a co-polymerizable photocrosslinker, and at least one initiator.

Also disclosed are methods of preparing adhesive articles. In some embodiments, the method comprises providing a substrate with a first major surface and a second major surface, providing a hot melt processable packaged adhesive composition, hot melt processing the packaged adhesive composition, disposing the hot melt processed packaged adhesive composition on at least a portion of the second major surface of the substrate to form a pressure sensitive adhesive layer, and photocrosslinking the pressure sensitive adhesive layer. The hot melt processable packaged adhesive composition is described above.

DETAILED DESCRIPTION

The use of adhesive products in the medical industry has long been prevalent, and is increasing. However, while medical adhesives and adhesive articles have shown themselves to be very useful for medical applications, there are also issues in the use of adhesives and adhesive articles. Medical adhesive-related skin injury (MARSI) has a significant negative impact on patient safety. Skin injury related to medical adhesive usage is a prevalent but under recognized complication that occurs across all care settings and among all age groups. In addition, treating skin damage is costly in terms of service provision, time, and additional treatments and supplies.

Skin Injury occurs when the superficial layers of the skin are removed along with the medical adhesive product, which not only affects skin integrity but can cause pain and the risk of infection, increase wound size, and delay healing, all of which reduce patients' quality of life.

Medical adhesive tape can be simply defined as a pressure-sensitive adhesive and a backing that acts as a carrier for the adhesive. The US Food and Drug Administration more specifically defines a medical adhesive tape or adhesive bandage as "a device intended for medical purposes that consists of a strip of fabric material or plastic, coated on one side with an adhesive, and may include a pad of surgical dressing without a disinfectant. The device is used to cover and protect wounds, to hold together the skin edges of a wound, to support an injured part of the body, or to secure objects to the skin."

While the pathophysiology of MARSI is only partially understood. S kin injury results when the skin cell to adhesive attachment is stronger than skin cell to skin cell attachment. When adhesive strength exceeds the strength of skin cell to skin cell interactions, cohesive failure occurs within the skin cell layer.

The intrinsic characteristics of all components of an adhesive product must then be taken into account to address these factors that may lead to MARSI. Properties of the adhesive to be considered include cohesiveness and the corresponding adhesion strength over time; properties of the tape/backing/dressing to be considered include breathability, stretch, conformability, flexibility, and strength.

The widespread use of adhesives in medical applications has led to the development of adhesives and adhesive articles that are gentle to the skin. Some of these adhesives are pressure sensitive adhesives. The application of pressure sensitive adhesives, including acrylate-based and silicone-based pressure sensitive adhesives, for adhering to skin is known in the art and many examples are commercially available. However, some pressure sensitive adhesives have issues that limit their use for adhesion to skin. For instance, skin damage may result during the removal of a pressure sensitive adhesive that exhibits strong interfacial adhesion between the adhesive and skin cells. Alternatively, if the adhesion to skin is reduced, the pressure sensitive adhesive may lack sufficient holding power to be useful. Additionally, some pressure sensitive adhesives, especially acrylate-based pressure sensitive adhesives that contain acidic or basic co-monomers, may lose skin adhesion significantly when they come into contact with bodily fluids that contain multivalent ions. Furthermore, some pressure sensitive adhesives that are relatively rigid or non-conformable compared to skin typically result in considerable patient discomfort during use. Also, even adhesives that have a measured low peel adhesion to skin may cause discomfort during removal, e.g., if the adhesive becomes surface attached around hair.

Thus, the need remains for adhesives suitable for medical uses that have high skin adhesion and high cohesive strength without causing skin damage upon removal. The medical adhesive also desirably maintains stable adhesion and adhesive holding power (often referred to as shear strength or shear holding power) during wear even when the adhesive articles come into contact with heavy body fluids.

Among the classes of adhesive materials that have found widespread use as pressure sensitive adhesives are (meth) acrylate-based pressure sensitive adhesives. These materials have many desirable features such as frequently being inherently tacky and thus not requiring the use of added tackifying agents, they are typically formed by free radical polymerization to a high conversion, meaning that little or no un-polymerized monomer is left in the formed pressure sensitive adhesive, and a wide range of monomers can be used to form (meth)acrylate-based copolymers to tailor the desired properties of the pressure sensitive adhesive. Frequently the (meth)acrylate-based pressure sensitive adhesive is prepared from a reaction mixture that contains acidic and basic monomers. Acidic and basic monomers are often classified in the adhesive arts as reinforcing monomers, as these monomers tend to increase the cohesive strength of (meth)acrylate-based pressure sensitive adhesives. However, acidic and basic monomers can be problematic in uses where the pressure sensitive adhesive can come into contact with human skin, especially when the adhesive comes into contact with heavy body fluids containing multivalent ions. Therefore, preparing (meth)acrylate-based pressure sensitive adhesives that retain the requisite cohesive strength to be useful in medical applications without including these acidic or basic reinforcing monomers is a challenge.

In some applications the requisite cohesive strength can be imparted to the pressure sensitive adhesive through the use of relatively high Tg monomers or monomers with crystalline groups. Often the reactions to form pressure sensitive adhesive polymers with these monomers must be carried out in a solution or dispersion and the formed adhesive polymer is delivered as a solution or dispersion. However, as pointed out below, as the adhesive industry has moved away from the use of solvents, the ongoing need is for adhesives that can be prepared and delivered without solvents.

Many classes of pressure sensitive adhesive have been prepared to address the increased need for performance issues. Often these pressure sensitive adhesives are provided as solutions or solvent-borne mixtures, often solutions or solvent-borne mixtures containing large amounts of solvents. Upon coating or dispensing, the solvent needs to be removed to produce an adhesive layer. Often the solvent is removed through the use of elevated temperature processing such as heating with an oven. Such solvent removal steps can add cost to the formed articles because solvent removal requires additional steps. Not only are additional steps involved, often these steps require specialized care, precautions and equipment because the solvents are volatile and generally flammable. In addition, shipment of adhesive solutions adds additional expense because of the added weight of solvent and may require special shipment precautions due to the presence of solvent. Environmental concerns are also an issue with solvent borne adhesive systems, since, even with the use of solvent reclamation equipment, solvent release to the environment is likely.

Therefore, 100% solids adhesive systems have been developed. Among the methods used to prepare 100% solids adhesive layers include curing-on-web systems, and hot melt processable adhesives. Each of these systems has drawbacks as well as advantages. In curing-on-web systems, frequently the level of residual monomers makes them undesirable or unusable in medical applications. Difficulties have also arisen when solvent processing has been replaced by hot melt processing. Often it is difficult to replicate the properties of solvent delivered adhesive layers with hot melt delivered systems, partially due to strong chain orientation that can develop in adhesive layers formed by extrusion processes.

Thus, among the desirable, and often contradictory, features desired for a medical adhesive include: high enough adhesion to attach to skin without causing skin damage upon removal; being free of acidic or basic monomers which can cause skin damage and/or skin irritation, and yet have sufficiently high cohesive strength to be useful; high skin adhesion but stable adhesion during wear, especially when the adhesive comes into contact with heavy body fluids; and being hot melt processable so that the use of solvents is not required.

Another challenge with using adhesive articles for medical applications is the ability of medical adhesive to maintain sufficient adhesion to skin during wear. Typically, the skin adhesion drops significantly when the adhesive is confronted with body fluids, e.g. sweat and/or saliva, due to the ionic crosslinking between adhesives containing either acid or base comonomers (e.g. AA (acrylic acid) or ACM rubbers) and multivalent ions from body fluids (e.g. $Ca^{2+}$ or $CO_3^{2-}$).

Among the attempts to provide adhesives with stable skin adhesion upon ageing is the use of rubber-based adhesives which do not contain acid/base functional groups in the adhesives, as described, for example, in JP Patent JP4849200. However, these rubber-based adhesives have other issues, such as they can cause significantly higher skin allergy and/or skin sensitivity due to a higher percentage of irritant, and these rubber-based adhesives typically have lower moisture transmission. Other attempts to provide stable skin adhesion upon aging involve the use non-polar acrylate adhesives, as described in U.S. Pat. No. 5,886,122. However, such adhesives lack cohesive strength due to lack of polarity, a drawback which is mitigated by a higher level of crosslinking. However, a higher level of crosslinking causes other issues, such as, it may decrease the adhesive strength of the adhesive.

Disclosed herein are adhesive articles, packaged adhesive compositions, and methods of preparing adhesive articles. The adhesive articles include a hot melt processable (meth) acrylate-based pressure sensitive adhesive, where the (meth) acrylate-based pressure sensitive adhesive is prepared from a reaction mixture that is free of acidic and basic monomers. The hot melt processable pressure sensitive adhesives are prepared as 100% solids compositions in a package surrounded by a packaging material, and these packages are able to be hot melt processed and disposed onto substrates to form adhesive articles.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein. The recitation of numerical ranges by endpoints includes all numbers subsumed within that range (e.g. 1 to 5 includes 1, 1.5, 2, 2.75, 3, 3.80, 4, and 5) and any range within that range.

As used in this specification and the appended claims, the singular forms "a", "an", and "the" encompass embodiments having plural referents, unless the content clearly dictates otherwise. For example, reference to "a layer" encompasses embodiments having one, two or more layers. As used in this specification and the appended claims, the term "or" is generally employed in its sense including "and/or" unless the content clearly dictates otherwise.

The term "adhesive" as used herein refers to polymeric compositions useful to adhere together two adherends. Examples of adhesives are pressure sensitive adhesives.

Pressure sensitive adhesive compositions are well known to those of ordinary skill in the art to possess properties including the following: (1) aggressive and permanent tack, (2) adherence with no more than finger pressure, (3) sufficient ability to hold onto an adherend, and (4) sufficient cohesive strength to be cleanly removable from the adherend. Materials that have been found to function well as pressure sensitive adhesives are polymers designed and formulated to exhibit the requisite viscoelastic properties resulting in a desired balance of tack, peel adhesion, and shear holding power. Obtaining the proper balance of properties is not a simple process.

The terms "Tg" and "glass transition temperature" are used interchangeably. If measured, Tg values can be determined by Differential Scanning calorimetry (DSC) at a scan rate of 10° C./minute, unless otherwise indicated. Tg values can also be measured using Dynamic Mechanical Analysis (DMA) as described in the Examples section. Typically, Tg values for copolymers are calculated using the well-known Fox Equation, using the monomer Tg values provided by the monomer supplier, as is understood by one of skill in the art.

The term "room temperature" refers to ambient temperature, generally 20-22° C., unless otherwise noted.

The term "(meth)acrylate" refers to monomeric acrylic or methacrylic esters of alcohols. Acrylate and methacrylate monomers or oligomers are referred to collectively herein as "(meth)acrylates". Polymers described as "(meth)acrylate-based" are polymers or copolymers prepared primarily (greater than 50% by weight) from (meth)acrylate monomers and may include additional ethylenically unsaturated monomers.

The term "adjacent" as used herein when referring to two layers means that the two layers are in proximity with one another with no intervening open space between them. They may be in direct contact with one another (e.g. laminated together) or there may be intervening layers.

The terms "polymer" and "macromolecule" are used herein consistent with their common usage in chemistry. Polymers and macromolecules are composed of many repeated subunits. As used herein, the term "macromolecule" is used to describe a group attached to a monomer that has multiple repeating units. The term "polymer" is used to describe the resultant material formed from a polymerization reaction.

The term "alkyl" refers to a monovalent group that is a radical of an alkane, which is a saturated hydrocarbon. The alkyl can be linear, branched, cyclic, or combinations thereof and typically has 1 to 20 carbon atoms. In some embodiments, the alkyl group contains 1 to 18, 1 to 12, 1 to 10, 1 to 8, 1 to 6, or 1 to 4 carbon atoms. Examples of alkyl groups include, but are not limited to, methyl, ethyl, n-propyl, isopropyl, n-butyl, isobutyl, tert-butyl, n-pentyl, n-hexyl, cyclohexyl, n-heptyl, n-octyl, and ethylhexyl.

The term "aryl" refers to a monovalent group that is aromatic and carbocyclic. The aryl can have one to five rings that are connected to or fused to the aromatic ring. The other ring structures can be aromatic, non-aromatic, or combinations thereof. Examples of aryl groups include, but are not limited to, phenyl, biphenyl, terphenyl, anthryl, naphthyl, acenaphthyl, anthraquinonyl, phenanthryl, anthracenyl, pyrenyl, perylenyl, and fluorenyl.

The term "alkylene" refers to a divalent group that is a radical of an alkane. The alkylene can be straight-chained, branched, cyclic, or combinations thereof. The alkylene often has 1 to 20 carbon atoms. In some embodiments, the alkylene contains 1 to 18, 1 to 12, 1 to 10, 1 to 8, 1 to 6, or 1 to 4 carbon atoms. The radical centers of the alkylene can be on the same carbon atom (i.e., an alkylidene) or on different carbon atoms.

The term "arylene" refers to a divalent group that is carbocyclic and aromatic. The group has one to five rings that are connected, fused, or combinations thereof. The other rings can be aromatic, non-aromatic, or combinations thereof. In some embodiments, the arylene group has up to 5 rings, up to 4 rings, up to 3 rings, up to 2 rings, or one aromatic ring. For example, the arylene group can be phenylene.

The term "heteroalkylene" refers to a divalent group that includes at least two alkylene groups connected by a thio, oxy, or —NR— where R is alkyl. The heteroalkylene can be linear, branched, cyclic, substituted with alkyl groups, or combinations thereof. Some heteroalkylenes are poloxyyalkylenes where the heteroatom is oxygen such as for example,

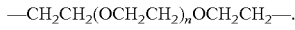

—CH$_2$CH$_2$(OCH$_2$CH$_2$)$_n$OCH$_2$CH$_2$—.

The terms "free radically polymerizable" and "ethylenically unsaturated" are used interchangeably and refer to a reactive group which contains a carbon-carbon double bond which is able to be polymerized via a free radical polymerization mechanism.

Disclosed herein are adhesive articles suitable for use in medical application. The articles comprise a substrate and a hot melt processable pressure sensitive adhesive disposed on at least a portion of the substrate. The substrate has a first major surface and a second major surface. Typically, the hot melt processable pressure sensitive adhesive is disposed on the first major surface of the substrate. As is described below, the substrate may be a monolithic construction or a multi-layer construction. In the multi-layer constructions, the substrate may have a variety or coatings or layers present either adjacent to or as the first or second surface of the substrate.

A wide range of substrates are suitable, including release liners, and medical substrates. Release liners are sheet materials that have a low adhesion coating on at least one surface. The hot melt processable pressure sensitive adhesives of the present disclosure can be disposed on a release liner to generate an article comprising a layer of pressure sensitive adhesive on a release liner. This adhesive/release liner article can be used to prepare other adhesive/substrate articles by laminating the adhesive layer to different substrate and then removing the release liner. This permits the adhesive to be disposed onto substrates to which it is difficult to directly dispose the hot melt processable pressure sensitive adhesive, such as substrates that are thermally sensitive. The adhesive/release liner article may also be used to apply the pressure sensitive adhesive layer to an article such as, for example, an electrode, an ostomy device, or the like.

Exemplary medical substrates include polymeric materials, plastics, natural macromolecular materials (e.g., collagen, wood, cork, silk, and leather), paper, cloth, fabrics, non-wovens, metals, glass, ceramics, composites, and combinations thereof. The medical substrate may be a tape backing. Examples of suitable tape backings include breathable conformable backing, on which the adhesive is disposed. A wide range of breathable conformable backings are suitable for use in articles of this disclosure. Typically, the breathable conformable backing comprises a woven or knit textile, a nonwoven, or a plastic.

In some embodiments, the breathable conformable backing comprises a high moisture vapor permeable film backing. Examples of such backings, methods of making such films, and methods for testing their permeability are described, for example, in U.S. Pat. Nos. 3,645,835 and 4,595,001. Typically, such backings are porous materials.

Generally, the backing is conformable to anatomical surfaces. As such, when the backing is applied to an anatomical surface, it conforms to the surface even when the surface is moved. Generally, the backing is also conformable to animal anatomical joints. When the joint is flexed and then returned to its unflexed position, the backing stretches to accommodate the flexion of the joint, but is resilient enough to continue to conform to the joint when the joint is returned to its unflexed condition.

Examples of particularly suitable backings can be found in U.S. Pat. Nos. 5,088,483 and 5,160,315, and include elastomeric polyurethane, polyester, or polyether block amide films. These films have a combination of desirable properties including resiliency, high moisture vapor permeability, and transparency.

The articles may include additional optional layers. In some embodiments, it may be desirable for there to be a primer layer between the substrate surface and the pressure sensitive adhesive layer. Generally, the primer layer comprises materials that are commonly referred to as "primers" or "adhesion promoters". Primers and adhesion promoters are materials that are applied as thin coatings on a surface and strongly adhere to the surface and provide a modified surface chemistry to the surface. Examples of suitable coating materials include polyamides, poly(meth)acrylates, chlorinated polyolefins, rubbers, chlorinated rubbers, polyurethanes, siloxanes, silanes, polyester, epoxies, polycarbodiimides, phenolics, and combinations thereof. Typically, the articles of this disclosure do not require primer layers since, when the hot melt processable pressure sensitive adhesives is disposed on the substrate surface it tends to form strong interactions with a wide range of substrate surfaces, making primers unnecessary.

In some embodiments, it may be desirable that the second major surface of the substrate, that is to say the surface on which the adhesive construction is not coated, have a low adhesion coating. This is especially true if the adhesive article is to be supplied in the form of a tape. Many tapes are supplied as rolls, where the adhesive layer contacts the non-adhesive "back" side of the backing upon being rolled up. Often this non-adhesive surface of the backing has a low adhesion or release coating on it to permit the roll to be unwound. These low adhesion coatings are often called "low adhesion backsizes" or LABs. Many factors control whether an LAB coating is necessary or desirable, including the nature of the adhesive, the composition and topography of the backing, and the desired use for the tape article.

The hot melt processable pressure sensitive adhesives of this disclosure comprise a (meth)acrylate-based copolymer that is the reaction product of a reaction mixture that is substantially free of acidic or basic monomers. The reaction mixture typically comprises as the polymerizable components, a first (meth)acrylate monomer that is present in a major amount, a second (meth)acrylate monomer present in a minor amount, and a co-polymerizable photocrosslinker. Each of these components is described in greater detail below.

The reaction mixture comprises a first (meth)acrylate monomer of general formula I:

$$CH_2=CR^1-(CO)-OR^2 \qquad \text{Formula I}$$

wherein $R^1$ is hydrogen or a methyl group, and $R^2$ is an alkyl, heteroalkyl, alkenyl, or aryl group. Alkyl (meth)acrylate monomers, ones where $R^2$ is an alkyl, are particularly suitable.

The first monomer is present in the reaction mixture in a major amount, meaning that greater than half of the reactive components in the reaction mixture comprise the first monomer. While the first monomer is referred to as a single material, of course the first monomer can a mixture of materials of the general structure of Formula I. Typically, the reaction mixture comprises 70-96 parts by weight of a first (meth)acrylate monomer of general Formula I. The term "parts by weight" is used to describe the quantity by weight of the reactive material present in the mixture. This term is similar to but is not to be confused with "weight %" or "% by weight". Typically, the components add up to total 100 parts by weight and thus parts by weight is the same as weight %, but in many embodiments the reactive components do not add up precisely to 100 parts by weight. In these embodiments, the term parts by weight are close to but not exactly the same as weight %. For example, a reactive mixture that includes 70 parts by weight of monomer 1, 30 parts by weight of monomer 2, and 0.1 parts by weight of monomer 3, has approximately 70 weight % monomer 1, but since the parts by weight of the monomers adds up to greater than 100, it is not correct to use that terminology.

As mentioned above, in some embodiments the first (meth)acrylate monomer is present in the amount of 70-96 parts by weight. In other embodiments, the first (meth)acrylate monomer is present in the amount of 80-96 parts by weight, and in yet other embodiments the first (meth)acrylate monomer is present in amounts of 90-96 parts by weight.

Useful alkyl (meth)acrylate monomers include monomeric acrylic or methacrylic acid esters of non-tertiary alkyl alcohols, the alkyl group of which comprises from about 1 to about 14 carbon atoms, in some embodiments from about 7 to about 9 carbon atoms, and mixtures thereof.

Suitable alkyl (meth)acrylate monomers include, but are not limited to, those selected from the group consisting of the esters of acrylic acid or methacrylic acid with non-tertiary alkyl alcohols such as 1-butanol, 1-pentanol, 2-pentanol, 3-pentanol, 2-methyl-1-butanol, 1-methyl-1-butanol, 1-methyl-1-pentanol, 2-methyl-1-pentanol, 3-methyl-1-pentanol, 2-ethyl-1-butanol, 2-ethyl-1-hexanol, 3,5,5-trimethyl-1-hexanol, 3-heptanol, 2-octanol, 1-decanol, 1-dodecanol, and the like, and mixtures thereof. Such monomeric acrylic or methacrylic esters are known in the art and are commercially available.

Generally, it is desirable that the first monomer have a relatively low homopolymer Tg. For this reason, in many embodiments, the first monomer frequently comprises an acrylate monomer instead of a methacrylate monomer, as acrylates tend to have lower homopolymer Tg values than their corresponding methacrylates. Homopolymer Tg is a characteristic, defining value for a monomer and refers to the Tg of a homopolymer of that monomer. Suppliers of acrylate and methacrylate monomers provide a homopolymer Tg value for the monomer, and this value can be used by one of skill in the art to determine the Tg of copolymers with that monomer by using the Fox equation. In some embodiments, the first monomer has a homopolymer Tg of −20° C. or lower.

Examples of particularly suitable alkyl acrylate monomers for use as the first (meth)acrylate monomer are isooctyl acrylate, 2-ethylhexyl acrylate, lauryl acrylate, isobutyl acrylate, and mixtures thereof.

The reaction mixture comprises a second (meth)acrylate monomer of general formula II:

$$CH_2=CR^1-(CO)-OR^3 \qquad \text{Formula II}$$

where $R^1$ is hydrogen or a methyl group, and $R^3$ is a hydroxyl substituted alkyl group, a hydroxyl substituted heterocyclic group, a hydroxyl substituted aryl group, or a hydroxyl substituted macromolecule.

Typically, the reaction mixture comprises 4-30 parts by weight of a second (meth)acrylate monomer of general Formula II. In some embodiments, the second (meth)acrylate monomer is present in the amount of 4-20 parts by weight, and in yet other embodiments the second (meth)acrylate monomer is present in amounts of 4-10 parts by weight.

Examples of suitable second monomers include those where the $R^3$ of the second monomer comprises a hydroxyl-substituted alkyl group comprising 2-6 carbon atoms, or a macromolecular group comprising a hydroxyl-terminated alkylene-oxide group. In some embodiments, the alkylene-oxide group comprises repeat units of the formula $-(R^4-O-)n-$, where $R^4$ is an alkyl group containing 2-4 carbon atoms, and n is an integer from 3-100.

Examples of particularly suitable alkyl acrylate monomers for use as the second (meth)acrylate monomer are 2-hydroxyethyl acrylate, hydroxylpropyl acrylate, 4-hydroxybutyl acrylate, and poly(ethylene glycol) acrylates.

The reaction mixture that forms the (meth)acrylate-based copolymer also comprises a co-polymerizable photocrosslinker. Co-polymerizable photocrosslinkers are materials that contain a free radically polymerizable group to co-polymerize with the monomers described above. The co-polymerizable photocrosslinkers also contain a photosensitive group that upon exposure to the right wavelength of light, typically high intensity ultra-violet (UV) radiation, the photosensitive group forms free radicals which can form crosslinks in the polymer. If the (meth)acrylate-based polymer is formed by the use of a photoinitiator, the photocrosslinker is not activated by the same wavelengths of light as the photoinitiator. In this way, the co-polymerizable photocrosslinker is incorporated into the polymer, and is able to be thermally processed, as the crosslinker is thermally stable and remains intact until activated by the proper wavelength of light. This permits the co-polymerizable photocrosslinker from becoming activated until the polymer has been hot melt coated. In some embodiments, these crosslinkers are activated by UV light generated from artificial sources such as medium pressure mercury lamps or a UV blacklight.

Suitable photocrosslinkers in the mono-ethylenically unsaturated aromatic ketone co-monomers that are free of ortho-aromatic hydroxyl groups such as those described in U.S. Pat. No. 4,737,559 (Kellen et al.). Specific examples include para-acryloxybenzophenone (ABP), para-acrylyoxyethoxybenzophenone, para-N-(methylacryloxyethyl)-carbamoylethoxybenzophenone, para-acryloxyacetophenone, ortho-acrylamidoacetophenone, acrylated anthraquinones, and the like. Particularly suitable is ABP para-acryloxybenzophenone also called 4-acryloxybenzophenone.

Typically, such photocrosslinkers are used in amounts of about 0.01 to 1.0 parts by weight of crosslinker per 100 parts by weight of total monomers present in the reaction mixture. In some embodiments, the photocrosslinker is present in amounts of about 0.10 parts by weight of crosslinker per 100 parts by weight of total monomers present in the reaction mixture.

The monomers are selected in such a way as to give the desired properties for the formed (meth)acrylate-based polymer. Since the (meth)acrylate-based copolymer is a pressure sensitive adhesive, it typically has a Tg that corresponds to room temperature (generally 20° C.) or lower. In some embodiments, the (meth)acrylate-based copolymer has a Tg of 0° C. or lower. In yet other embodiments, the (meth)acrylate-based copolymer has a Tg of −20° C. or lower. Typically, as is understood by one of skill in the adhesive arts, lower Tg adhesives have a lower modulus and thus tend to have improved wetting to highly textured surfaces such as skin.

The (meth)acrylate-based copolymer can have a wide range of molecular weights. Typically, the (meth)acrylate-based copolymer has a weight average molecular weight of 500,000 grams/mole or greater. This molecular weight is particularly suitable for hot melt processing. One way to increase molecular weight is to incorporate polymer branching with the addition of both difunctional (meth)acrylate comonomers (e.g. 1,6-Hexanediol diacrylate, or HDDA) and a free radical chain transfer agent (e.g. Iso-Octyl Thioglycolate, or IOTG).

As mentioned above, the reaction mixture from which the (meth)acrylate-based copolymer is formed contains a photocrosslinker. Typically, after the (meth)acrylate-based copolymer has been hot melt coated onto the substrate the (meth)acrylate-based copolymer is photocrosslinked. Typically, this photocrosslinking is carried out by exposure of the (meth)acrylate-based copolymer adhesive layer to UV radiation. The photocrosslinking is carried out on the coated adhesive layer to permit hot melt processing of the polymer, if the material were crosslinked prior to hot melt processing, the polymer would become either difficult or impossible to hot melt process. As mentioned above, the photocrossslinker is selected to be thermally stable to permit hot melt processing, and also to not activate at the same wavelength as the photoinitiator, if a photoinitiator is used to form the (meth)acrylate-based copolymer.

The pressure sensitive adhesive layer may be of any suitable thickness, depending upon the desired use. In some embodiments, the thickness will be at least 10 micrometers, up to 2 millimeters, and in some embodiments the thickness will be at least 20 micrometers up to 1 millimeter thick. A wide range of intermediate thicknesses are also suitable, such as 25-500 micrometers, 200-400 micrometers, and the like.

Besides the (meth)acrylate-based copolymer, the pressure sensitive adhesive layer may further comprise one or more additives. A wide variety of additives are suitable as long as the additives do not hinder the utility of the pressure sensitive adhesive layer in medical articles. The additives can be added to the reaction mixture as long as the additives do not interfere with the polymerization reaction. Additionally, additives can be added to the (meth)acrylate-based copolymer during hot melt processing.

As will be explained in detail below, typically the (meth)acrylate-based copolymer is polymerized within a package. This package, upon polymerization, contains the (meth)acrylate-based copolymer, and also may contain optional additives. Generally, these packages are placed into a hot melt extruder and ground up to form the pressure sensitive adhesive, which is coated onto the substrate to form the adhesive article.

One artifact of this process is that hot melt processing of the packaged adhesive generates particles of the packaging material in the pressure sensitive adhesive layer. Therefore, in many embodiments, the pressure sensitive adhesive further comprises particles formed from the packaging material which is a thermoplastic polymer. A wide variety of thermoplastic polymers are suitable. Examples of suitable thermoplastic polymers include polyethylene, ethylene vinyl acetate, ethylene methyl acrylate, ethylene acrylic acid, ethylene acrylic acid ionomers, polypropylene, acrylic polymers, polyphenylene ether, polyphenylene sulfide, acrylonitrile-butadiene-styrene copolymers, polyurethanes, and mixtures and blends thereof.

Examples of other suitable optional additives that can be included in the pressure sensitive adhesive layer include tackifying resins, plasticizers, anti-oxidants, fillers, leveling agents, ultraviolet light absorbers, hindered amine light stabilizers (HALS), oxygen inhibitors, wetting agents, rheology modifiers, defoamers, biocides, dyes, pigments, and the like. All of these additives and the use thereof are well known in the art. It is understood that any of these compounds can be used so long as they do not deleteriously affect the adhesive properties.

In many embodiments of this disclosure, the hot melt processable adhesive comprises a hot melt processable packaged adhesive composition. Methods for preparing hot melt processable packaged adhesive compositions are described in U.S. Pat. No. 5,804,610 (Hamer et al.). The hot melt processable packaged adhesive compositions of this disclosure comprise a hot melt processable adhesive comprising a polymerized (meth)acrylate-based copolymer formed from a polymerizable pre-adhesive mixture, and a packaging material. These pre-adhesive mixtures are substantially free of acidic or basic monomers.

The pre-adhesive mixture typically comprises, a first (meth)acrylate monomer that is present in a major amount, a second (meth)acrylate monomer present in a minor amount, a co-polymerizable photocrosslinker, and at least one initiator. In some embodiments, the pre-adhesive composition contains other components such as a chain transfer agent and/or a di-functional (meth)acrylate. Each of these components is described in greater detail below.

The pre-adhesive mixture comprises a first (meth)acrylate monomer of general Formula I:

$$CH_2=CR^1-(CO)-OR^2 \quad \text{Formula I}$$

wherein $R^1$ is hydrogen or a methyl group, and $R^2$ is an alkyl, heteroalkyl, alkenyl, or aryl group. Alkyl (meth)acrylate monomers, ones where $R^2$ is an alkyl, are particularly suitable.

The first monomer is present in the pre-adhesive mixture in a major amount, meaning that greater than half of the reactive components in the pre-adhesive mixture comprise the first monomer. While the first monomer is referred to as a single material, of course the first monomer can a mixture of materials of the general structure of Formula I. Typically, the pre-adhesive mixture comprises 70-96 parts by weight of a first (meth)acrylate monomer of general Formula I.

As mentioned above, in some embodiments the first (meth)acrylate monomer is present in the amount of 70-96 parts by weight. In other embodiments, the first (meth)acrylate monomer is present in the amount of 80-96 parts by weight, and in yet other embodiments the first (meth)acrylate monomer is present in amounts of 90-96 parts by weight.

Useful alkyl (meth)acrylate monomers include monomeric acrylic or methacrylic acid esters of non-tertiary alkyl alcohols, the alkyl group of which comprises from about 1 to about 14 carbon atoms, in some embodiments from about 7 to about 9 carbon atoms, and mixtures thereof.

Suitable alkyl (meth)acrylate monomers include, but are not limited to, those selected from the group consisting of the esters of acrylic acid or methacrylic acid with non-tertiary alkyl alcohols such as 1-butanol, 1-pentanol, 2-pentanol, 3-pentanol, 2-methyl-1-butanol, 1-methyl-1-butanol, 1-methyl-1-pentanol, 2-methyl-1-pentanol, 3-methyl-1-pentanol, 2-ethyl-1-butanol, 2-ethyl-1-hexanol, 3,5,5-trimethyl-1-hexanol, 3-heptanol, 2-octanol, 1-decanol, 1-dodecanol, and the like, and mixtures thereof. Such monomeric acrylic or methacrylic esters are known in the art and are commercially available.

Generally, it is desirable that the first monomer have a relatively low homopolymer Tg. For this reason, in many embodiments, the first monomer frequently comprises an acrylate monomer instead of a methacrylate monomer, as acrylates tend to have lower homopolymer Tg values than their corresponding methacrylates. In some embodiments, the first monomer has a homopolymer Tg of −20° C. or lower.

Examples of particularly suitable alkyl acrylate monomers for use as the first (meth)acrylate monomer are isooctyl acrylate, 2-ethylhexyl acrylate, lauryl acrylate, isobutyl acrylate, and mixtures thereof.

The pre-adhesive mixture comprises a second (meth)acrylate monomer of general Formula II:

$$CH_2=CR^1-(CO)-OR^3 \qquad \text{Formula II}$$

where $R^1$ is hydrogen or a methyl group, and $R^3$ is a hydroxyl substituted alkyl group, a hydroxyl substituted heterocyclic group, a hydroxyl substituted aryl group, or a hydroxyl substituted macromolecule.

Typically, the pre-adhesive mixture comprises 4-30 parts by weight of a second (meth)acrylate monomer of general Formula II. In some embodiments, the second (meth)acrylate monomer is present in the amount of 4-20 parts by weight, and in yet other embodiments the second (meth)acrylate monomer is present in amounts of 4-10 parts by weight.

Examples of suitable second monomers include those where the $R^3$ of the second monomer comprises a hydroxyl-substituted alkyl group comprising 2-6 carbon atoms, or a macromolecular group comprising a hydroxyl-terminated alkylene-oxide group. In some embodiments, the alkylene-oxide group comprises repeat units of the formula $-(R^4-O-)_n-$, where $R^4$ is an alkyl group containing 2-4 carbon atoms, and n is an integer from 3-100.

Examples of particularly suitable alkyl acrylate monomers for use as the second (meth)acrylate monomer are 2-hydroxyethyl acrylate, hydroxylpropyl acrylate, 4-hydroxybutyl acrylate, and poly(ethylene glycol) acrylates.

The pre-adhesive mixture that forms the (meth)acrylate-based copolymer also comprises a co-polymerizable photocrosslinker, as described above. Co-polymerizable photocrosslinkers are materials that contain a free radically polymerizable group to co-polymerize with the monomers described above. The co-polymerizable photocrosslinkers also contain a photosensitive group that upon exposure to the right wavelength of light, typically high intensity ultraviolet (UV) radiation, the photosensitive group forms free radicals which can form crosslinks in the polymer. If the (meth)acrylate-based polymer is formed by the use of a photoinitiator, the photocrosslinker is not activated by the same wavelengths of light as the photoinitiator. In this way, the co-polymerizable photocrosslinker is incorporated into the polymer, and is able to be thermally processed, as the crosslinker is thermally stable and remains intact until activated by the proper wavelength of light. This permits the co-polymerizable photocrosslinker from becoming activated until the polymer has been hot melt coated. In some embodiments, these crosslinkers are activated by UV light generated from artificial sources such as medium pressure mercury lamps or a UV blacklight.

Suitable photocrosslinkers in the mono-ethylenically unsaturated aromatic ketone comonomers that are free of ortho-aromatic hydroxyl groups such as those described in U.S. Pat. No. 4,737,559 (Kellen et al.). Specific examples include para-acryloxybenzophenone (ABP), para-acrylyoxyethoxybenzophenone, para-N-(methylacryloxyethyl)-carbamoylethoxybenzophenone, para-acryloxyacetophenone, ortho-acrylamidoacetophenone, acrylated anthraquinones, and the like. Particularly suitable is ABP para-acryloxybenzophenone also called 4-acryloxybenzophenone.

Typically, such photocrosslinkers are used in amounts of about 0.01 to 1.0 parts by weight of crosslinker per 100 parts by weight of total monomers present in the reaction mixture. In some embodiments, the photocrosslinker is present in amounts of about 0.10 parts by weight of crosslinker per 100 parts by weight of total monomers present in the reaction mixture.

The pre-adhesive mixture also comprises at least one initiator. Typically, the initiator is a photoinitiator, meaning that the initiator is activated by light, typically ultraviolet (UV) light. Photoinitiators are well understood by one of skill in the art of (meth)acrylate polymerization. Examples of suitable free radical photoinitiators include DAROCURE 1173, DAROCURE 4265, IRGACURE 184, IRGACURE 651, IRGACURE 1173, IRGACURE 819, LUCIRIN TPO, LUCIRIN TPO-L, commercially available from BASF, Charlotte, NC. The photoinitiator DAROCURE 1173 is particularly suitable.

Generally, the photoinitiator is used in amounts of 0.01 to 2 parts by weight, more typically 0.1 to 0.5, parts by weight relative to 100 parts by weight of total reactive components.

The pre-adhesive mixture may also comprise a variety of optional additives as long as the additives do not adversely affect the polymerization reaction. One particularly suitable additive is a chain transfer agent. Examples of useful chain transfer agents include, but are not limited to, those selected from the group consisting of carbon tetrabromide, mercaptans, alcohols, and mixtures thereof. A particularly suitable chain transfer agent is IOTG (isooctyl thioglycolate). Chain transfer agents and the use of chain transfer agents is well understood in the adhesive arts.

The components of the pre-adhesive mixture are selected in such a way as to give the desired properties for the formed hot melt processable (meth)acrylate-based polymer. Since the hot melt processable (meth)acrylate-based copolymer is a pressure sensitive adhesive, it typically has a Tg that corresponds to room temperature (generally 20° C.) or lower. In some embodiments, the (meth)acrylate-based copolymer has a Tg of 0° C. or lower. In yet other embodiments, the (meth)acrylate-based copolymer has a Tg of −20° C. or lower.

The hot melt processable (meth)acrylate-based copolymer can have a wide range of molecular weights. Typically, the (meth)acrylate-based copolymer has a weight average molecular weight of 500,000 grams/mole or greater. This molecular weight is particularly suitable for hot melt processing.

The hot melt processable packaged adhesive composition also comprises a packaging material. The packaging material completely surrounds the polymerized pre-adhesive mixture and any optional additives. The packaging material is a thermoplastic material that generally melts at or below the processing temperature of the polymerized pre-adhesive mixture (in other words, the temperature at which the polymerized pre-adhesive mixture flows). The packaging material generally has a melting point of 200° C. or less, or 170° C. or less. In some embodiments the melting point ranges from 90° C. to 150° C. The packaging material may be a flexible thermoplastic polymeric film. The flexible thermoplastic polymeric films are prepared from thermoplastic materials. Suitable thermoplastic materials include polyethylene, and ethylene copolymers such as ethylene/polyolefin copolymers and ethylene/vinyl copolymers such as ethylene vinyl acetate (EVA), ethylene methyl acrylate (EMA), ethylene acrylic acid (EAA), EAA ionomers, and polypropylene, and other thermoplastic materials such as acrylics, polyphenylene ether, polyphenylene sulfide, acrylonitrile-butadiene-styrene copolymer (ABS), polyurethanes, and others know to those skilled in the art. Blends of thermoplastic materials may also be used. Particularly suitable thermoplastic materials are polyethylene and EVA.

The flexible thermoplastic films range in thickness from 0.01 mm to 0.25 mm. The thicknesses typically range from 0.025 mm to 0.127 mm to obtain films that have good strength during processing while being thin enough to heat seal quickly and minimize the amount of film material used.

The packaging materials may contain plasticizers, stabilizers, dyes, perfumes, fillers, slip agents, antiblock agents, flame retardants, anti-static agents, microwave susceptors, thermally conductive particles, electrically conductive particles, and/or other materials to increase the flexibility, handleability, visibility, or other useful property of the film, as long as they do not adversely affect the desired properties of the adhesive composition.

The amount of packaging material depends upon the type of material and the desired end properties. The amount of packaging material typically ranges from 0.5 to 20 weight % based on the total weight of the adhesive composition and the packaging material. Typically, the packaging material is between 2 and 15 weight %, and more typically between 3 and 5 weight %.

Also disclosed are methods for preparing adhesive articles. In some embodiments, the method comprises providing a substrate with a first major surface and a second major surface, providing a hot melt processable packaged adhesive composition, hot melt processing the packaged adhesive composition, disposing the hot melt processed packaged adhesive composition on at least a portion of the first major surface of the substrate to form a pressure sensitive adhesive layer, and photocrosslinking the pressure sensitive adhesive layer.

Suitable substrates are described above. A wide range of substrates are suitable, including release liners, and medical substrates. Release liners are sheet materials that have a low adhesion coating on at least one surface. The hot melt processable pressure sensitive adhesives of the present disclosure can be disposed on a release liner to generate an article comprising a layer of pressure sensitive adhesive on a release liner. This adhesive/release liner article can be used to prepare other adhesive/substrate articles by laminating the adhesive layer to different substrate and then removing the release liner. This permits the adhesive to be disposed onto substrates to which it is difficult to directly dispose the hot melt processable pressure sensitive adhesive. The adhesive/release liner article may also be used to apply the pressure sensitive adhesive layer to an article such as, for example, an electrode, an ostomy device, or the like.

Exemplary medical substrates include polymeric materials, plastics, natural macromolecular materials (e.g., collagen, wood, cork, silk, and leather), paper, cloth, fabrics, non-wovens, metals, glass, ceramics, composites, and combinations thereof. The medical substrate may be a tape backing. Examples of suitable tape backings include breathable conformable backing, on which the adhesive is disposed. A wide range of breathable conformable backings are suitable for use in articles of this disclosure. Typically, the breathable conformable backing comprises a woven or knit textile, a nonwoven, or a plastic.

Hot melt processable packaged adhesive compositions are described above in detail and comprise the hot melt processable (meth)acrylate based copolymer and a packaging material.

The hot melt processable packaged adhesive composition is hot melt processed and disposed on the second major surface of the substrate. Methods of preparing hot melt processable packaged adhesive compositions are described in detail below. These packaged adhesive compositions are hot melt processed through the use of a hot melt mixing apparatus. Besides the hot melt processable packaged adhesive composition, optional additives can be added to the hot melt mixture at this point if desired. Typically, in embodiments of this disclosure, optional additives are not added.

A variety of hot melt mixing techniques using a variety of hot melt mixing equipment are suitable for processing the packaged adhesive compositions. Both batch and continuous mixing equipment may be used. Examples of batch methods include those using a BRABENDER (e.g. a BRABENDER PREP CENTER, commercially available from C. W. Brabender Instruments, Inc.; South Hackensack, NJ) or BANBURY internal mixing and roll milling equipment (e.g. equipment available from Farrel Co.; Ansonia, CN). Examples of continuous methods include single screw extruding, twin screw extruding, disk extruding, reciprocating single screw extruding, and pin barrel single screw extruding. Continuous methods can utilize distributive elements, pin mixing elements, static mixing elements, and dispersive elements such as MADDOCK mixing elements and SAXTON mixing elements. A single hot melt mixing apparatus may be used, or a combination of hot melt mixing equipment may be used to process the packaged adhesive compositions of this disclosure.

The output of the hot melt mixing is coated onto the substrate to form an adhesive layer. If a batch apparatus is used, the resulting hot melt blend can be removed from the apparatus and placed in a hot melt coater or extruder and coated onto a substrate. If an extruder is used to prepare a hot melt blend, the blend can be directly extruded onto a substrate to form an adhesive layer in a continuous forming method. In the continuous forming method, the adhesive can be drawn out of a film die and subsequently contacted to the substrate surface.

To crosslink the pressure sensitive adhesive layer, the adhesive layer is subjected to a photocrosslinking process. In this process, the photosensitive crosslinker is activated by exposure to high intensity UV lamps to effect crosslinking. Examples of suitable UV lamps include medium pressure mercury lamps.

The hot melt processable packaged adhesive compositions can be prepared using methods describe in, for example, U.S. Pat. No. 6,294,249 (Hamer et al.). In this method, a polymerizable pre-adhesive composition is prepared. The polymerizable pre-adhesive mixture comprises a first (meth)acrylate monomer of general Formula I, a second (meth)acrylate monomer of general Formula II, a photocrosslinking agent, a polymerization initiator, and optional additives, such as chain transfer agents. This mixture can be prepared and mixed in any suitable mixing apparatus. Each of these components is described in detail above.

In some embodiments, two lengths of thermoplastic film are heat sealed together across the bottom and on each of the lateral edges on a liquid form-fill-seal machine to form an open ended pouch. The pre-adhesive composition is pumped through a hose to fill the pouch, and the pouch is then heat sealed across the top to completely surround the adhesive composition.

Generally, the form-fill-seal machine is equipped with an impulse sealer to form the top and bottom seal across the pouches. Such a sealer has one or two sets of jaws that clamp the pouch shut before sealing. A sealing wire is then heated to effect the seal, and the seal is cooled before the jaws are released. The sealing temperature is generally above the softening point and below the melting point of the film used to form the pouch.

During the sealing process, it is desirable to get most of the air out of the pouch before sealing. A small amount of air is tolerable so long as the amount of oxygen is not sufficient to substantially interfere with the polymerization process. For ease of handling, it is desirable to seal the pouches as soon as they are filled with the composition, although immediate sealing is not necessary in all cases. In some cases, the pre-adhesive composition can alter the packaging material, and it is desirable to cross-seal the pouches within about one minute of filling, more typically within 30 seconds, and most typically within 15 seconds. If the pre-adhesive composition decreases the strength of the packaging material, it is desirable to polymerize the composition as soon as possible after the pre-adhesive composition is surrounded by the packaging material.

Alternatively, a single length of film can be folded lengthwise and sealed on one edge, filled with the pre-adhesive composition, and sealed. In another embodiment, a single length of film can be pulled through a forming collar, sealed to form a tube, filled with the composition, and sealed. Another embodiment can be carried out on commercial liquid form-fill-seal machines. A source of such machines is the Packaging Machinery Division of Eagle Corp. It is contemplated that the seals can be effected in any of a number of different configurations to form multiple pouches across and down the lengths of film. For example, in addition to the seals on the lateral edges, a seal can also be formed down the center of the lengths of film so that a cross seal will form two filled pouches. The pouches can either be left attached to each other by the cross-seals and/or vertical seals, or they can be cut into individual pouches or strands of pouches. The pouches may each contain the same or different compositions.

Typically, the pre-adhesive composition is polymerized by activation of the photoinitiator by radiation of the appropriate wavelength, typically UV radiation. In many embodiments, the packaged pre-adhesive composition is immersed in a heat exchange medium to moderate the generation of excessive heat during the polymerization. In many embodiments, the heat exchange medium is water maintained at room temperature.

Upon completion of the polymerization, a packaged adhesive composition is generated. This packaged adhesive composition can be used immediately, stored for later use, or shipped to a different location for hot melt processing. Because the viscoelastic adhesive composition is contained within a package, handling and storage is greatly simplified. Suitable packaging material are thermoplastic polymers and are described in detail above.

The disclosure includes the flowing embodiments:

The disclosure includes adhesive articles, packaged adhesive compositions, and methods for preparing adhesive articles.

Among the embodiments are adhesive articles. Embodiment 1 includes an article comprising: a substrate; and a hot melt processable pressure sensitive adhesive disposed on at least a portion of the substrate, the hot melt processable pressure sensitive adhesive comprising a (meth)acrylate-based copolymer that is the reaction product of a reaction mixture that is substantially free of acidic or basic monomers and comprising as the polymerizable components: 70-96 parts by weight of a first (meth)acrylate monomer of general Formula I:

$$CH_2=CR^1-(CO)-OR^2 \qquad \text{Formula I}$$

wherein $R^1$ is hydrogen or a methyl group; and $R^2$ is an alkyl, heteroalkyl, alkenyl, or aryl group; and 4-30 parts by weight of a second (meth)acrylate monomer of general Formula II:

$$CH_2=CR^1-(CO)-OR^3 \qquad \text{Formula II}$$

wherein $R^1$ is hydrogen or a methyl group; and $R^3$ is a hydroxyl substituted alkyl group, a hydroxyl substituted heterocyclic group, a hydroxyl substituted aryl group, or a hydroxyl substituted macromolecule; and a co-polymerizable photocrosslinker.

Embodiment 2 is the article of embodiment 1, wherein the pressure sensitive adhesive further comprises particles of a thermoplastic polymer, wherein the thermoplastic polymer comprises polyethylene, ethylene vinyl acetate, ethylene methyl acrylate, ethylene acrylic acid, ethylene acrylic acid ionomers, polypropylene, acrylic polymers, polyphenylene ether, polyphenylene sulfide, acrylonitrile-butadiene-styrene copolymers, polyurethanes, and mixtures and blends thereof.

Embodiment 3 is the article of embodiment 1 or 2, wherein the substrate comprises a polymeric film, a fabric, a non-woven, a foam, a paper, a mesh, an adhesive, or a release liner.

Embodiment 4 is the article of any of embodiments 1-3, wherein the reaction mixture comprises 80-96 parts by weight of the first monomer, and 4-20 parts by weight of the second monomer.

Embodiment 5 is the article of any of embodiments 1-4, wherein the reaction mixture comprises 90-96 parts by weight of the first monomer, and 4-10 parts by weight of the second monomer.

Embodiment 6 is the article of any of embodiments 1-5, wherein the (meth)acrylate-based copolymer has a Tg of −20° C. or lower.

Embodiment 7 is the article of any of embodiments 1-6, wherein the (meth)acrylate-based copolymer has a weight average molecular weight Mw of 500,000 grams/mole or greater.

Embodiment 8 is the article of any of embodiments 1-7, wherein the first monomer has a homopolymer Tg of −20° C. or lower.

Embodiment 9 is the article of any of embodiments 1-8, wherein the $R^2$ of the first monomer is an alkyl group having 1 to 14 carbon atoms.

Embodiment 10 is the article of any of embodiments 1-9, wherein the $R^2$ of the first monomer is an alkyl group having 7 to 9 carbon atoms.

Embodiment 11 is the article of any of embodiments 1-10, wherein the first monomer is selected from a group comprising isooctyl acrylate, 2-ethylhexyl acrylate, lauryl acrylate, isobutyl acrylate, and mixtures thereof.

Embodiment 12 is the article of any of embodiments 1-11, wherein the $R^3$ of the second monomer comprises: a hydroxyl-substituted alkyl group comprising 2-6 carbon atoms; or a macromolecular group comprising a hydroxyl-terminated alkylene-oxide group, wherein the alkylene-oxide group comprises repeat units of the formula —($R^4$—O-)n-, where $R^4$ is an alkyl group containing 2-4 carbon atoms, and n is an integer from 3-100.

Embodiment 13 is the article of any of embodiments 1-12, wherein the second monomer is 2-hydroxyethyl acrylate, hydroxylpropyl acrylate, or 4-hydroxybutyl acrylate.

Embodiment 14 is the article of any of embodiments 1-13, wherein the pressure sensitive adhesive layer further comprises at least one additive.

Embodiment 15 is the article of embodiment 14, wherein the additive comprises an anti-oxidant.

Embodiment 16 is the article of any of embodiments 1-15, wherein the pressure sensitive adhesive layer has been photocrosslinked.

Also disclosed are packaged adhesive compositions. Embodiment 17 includes a packaged adhesive composition comprising: a hot melt processable adhesive comprising a polymerized (meth)acrylate-based copolymer formed from a polymerizable pre-adhesive mixture, wherein the polymerizable pre-adhesive mixture composition is substantially free of acidic or basic monomers and comprises: 70-96 parts by weight of a first (meth)acrylate monomer of general formula I:

$$CH_2=CR^1-(CO)-OR^2 \quad \text{Formula I}$$

wherein $R^1$ is hydrogen or a methyl group; and $R^2$ is an alkyl, heteroalkyl, alkenyl, or aryl group; and 4-30 parts by weight of a second (meth)acrylate monomer of general Formula II:

$$CH_2=CR^1-(CO)-OR^3 \quad \text{Formula II}$$

wherein $R^1$ is hydrogen or a methyl group; and $R^3$ is a hydroxyl substituted alkyl group, a hydroxyl substituted heterocyclic group, a hydroxyl substituted aryl group, or a hydroxyl substituted macromolecule; a co-polymerizable photocrosslinker; and at least one initiator; and a packaging material.

Embodiment 18 is the packaged adhesive composition of embodiment 17, wherein the polymerizable pre-adhesive mixture composition further comprises a chain transfer agent.

Embodiment 19 is the packaged adhesive composition of embodiment 17 or 18, wherein the polymerizable pre-adhesive mixture composition comprises 80-96 parts by weight of the first monomer, and 4-20 parts by weight of the second monomer.

Embodiment 20 is the packaged adhesive composition of any of embodiments 17-19, wherein the polymerizable pre-adhesive mixture composition comprises 90-96 parts by weight of the first monomer, and 4-10 parts by weight of the second monomer.

Embodiment 21 is the packaged adhesive composition of any of embodiments 17-20, wherein the polymerized (meth)acrylate-based copolymer has a Tg of −20° C. or lower.

Embodiment 22 is the packaged adhesive composition of any of embodiments 17-21, wherein the polymerized (meth)acrylate-based copolymer has a weight average molecular weight Mw of 500,000 grams/mole or greater.

Embodiment 23 is the packaged adhesive composition of any of embodiments 17-22, wherein the first monomer has a homopolymer Tg of −20° C. or lower.

Embodiment 24 is the packaged adhesive composition of any of embodiments 17-23, wherein the $R^2$ of the first monomer is an alkyl group having 1 to 14 carbon atoms.

Embodiment 25 is the packaged adhesive composition of any of embodiments 17-24, wherein the $R^2$ of the first monomer is an alkyl group having 7 to 9 carbon atoms.

Embodiment 26 is the packaged adhesive composition of any of embodiments 17-25, wherein the first monomer is selected from a group comprising isooctyl acrylate, 2-ethylhexyl acrylate, lauryl acrylate, isobutyl acrylate, and mixtures thereof.

Embodiment 27 is the packaged adhesive composition of any of embodiments 17-26, wherein the $R^3$ of the second monomer comprises: a hydroxyl-substituted alkyl group comprising 2-6 carbon atoms; or a macromolecular group comprising a hydroxyl-terminated alkylene-oxide group, wherein the alkylene-oxide group comprises repeat units of the formula —($R^4$—O-)n-, where $R^4$ is an alkyl group containing 2-4 carbon atoms, and n is an integer from 3-100.

Embodiment 28 is the packaged adhesive composition of any of embodiments 17-27, wherein the second monomer is 2-hydroxyethyl acrylate, hydroxylpropyl acrylate, or 4-hydroxybutyl acrylate.

Embodiment 29 is the packaged adhesive composition of any of embodiments 17-28, wherein the pressure sensitive adhesive further comprises at least one additive.

Embodiment 30 is the packaged adhesive composition of any of embodiments 17-29, wherein the packaging material comprises a thermoplastic polymer, wherein the thermoplastic polymer comprises polyethylene, ethylene vinyl acetate, ethylene methyl acrylate, ethylene acrylic acid, ethylene acrylic acid ionomers, polypropylene, acrylic polymers, polyphenylene ether, polyphenylene sulfide, acrylonitrile-butadiene-styrene copolymers, polyurethanes, and mixtures and blends thereof.

Also disclosed are methods of preparing adhesive articles. Embodiment 31 includes a method of preparing an adhesive article comprising: providing a substrate with a first major surface and a second major surface; providing a hot melt processable packaged adhesive composition comprising: a hot melt processable adhesive comprising a polymerized (meth)acrylate-based copolymer formed from a polymerizable pre-adhesive mixture, wherein the polymerizable pre-adhesive mixture composition is substantially free of acidic or basic monomers and comprises: 70-96 parts by weight of a first (meth)acrylate monomer of general Formula I:

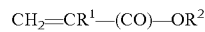

$$CH_2=CR^1-(CO)-OR^2 \quad \text{Formula I}$$

wherein $R^1$ is hydrogen or a methyl group; and $R^2$ is an alkyl, heteroalkyl, alkenyl, or aryl group; and 4-30 parts by weight of a second (meth)acrylate monomer of general Formula II:

$$CH_2=CR^1-(CO)-OR^3 \qquad \text{Formula II}$$

wherein $R^1$ is hydrogen or a methyl group; and $R^3$ is a hydroxyl substituted alkyl group, a hydroxyl substituted heterocyclic group, a hydroxyl substituted aryl group, or a hydroxyl substituted macromolecule; a co-polymerizable photocrosslinker; and at least one initiator; and a packaging material; hot melt processing the packaged adhesive composition; disposing the hot melt processed packaged adhesive composition on at least a portion of the second major surface of the substrate to form a pressure sensitive adhesive layer; and photocrosslinking the pressure sensitive adhesive layer.

Embodiment 32 is the method of embodiment 31, wherein the packaging material comprises polyethylene, ethylene vinyl acetate, ethylene methyl acrylate, ethylene acrylic acid, ethylene acrylic acid ionomers, polypropylene, acrylic polymers, polyphenylene ether, polyphenylene sulfide, acrylonitrile-butadiene-styrene copolymers, polyurethanes, and mixtures and blends thereof.

Embodiment 33 is the method of embodiment 31 or 32, wherein the polymerizable pre-adhesive mixture further comprises a chain transfer agent.

Embodiment 34 is the method of any of embodiments 31-33, wherein polymerized (meth)acrylate-based copolymer comprises polymerizing the polymerizable pre-adhesive mixture by activation of the initiator.

Embodiment 35 is the method of any of embodiments 31-34, wherein the initiator comprises a photoinitiator.

Embodiment 36 is the method of any of embodiments 31-35, wherein crosslinking comprises photochemical initiation of the co-polymerizable photocrosslinker.

Embodiment 37 is the method of any of embodiments 31-36, wherein the pressure sensitive adhesive layer further comprises at least one additive.

Examples

These examples are merely for illustrative purposes only and are not meant to be limiting on the scope of the appended claims. All parts, percentages, ratios, etc. in the examples and the rest of the specification are by weight, unless noted otherwise. Solvents and other reagents used were obtained from Sigma-Aldrich Chemical Company; Milwaukee, Wisconsin unless otherwise noted. The following abbreviations are used: mm=millimeters; cm= centimeters; in=inch; mL=milliliters; μg=micrograms; kg= kilograms; lb=pounds; Pa=Pascals; min=minutes; ppm=parts per million.

Materials

| | |
|---|---|
| IOA | Isooctyl acrylate, monomer; available from Sigma-Aldrich (St. Louis, MO) |
| EHA | 2-Ethylhexyl acrylate, monomer; available from Sigma-Aldrich (St. Louis, MO) |
| HEA | 2-Hydroxyethyl acrylate, monomer; available from KOWA American Corporation (New York, NY) |
| HPA | Hydroxypropyl acrylate, monomer; available from KOWA American Corporation (New York, NY) |
| RBA | 4-Hydroxybutyl acrylate, monomer; available from KOWA American Corporation (New York, NY) |
| 2-PHA | 2-propylheptyl acrylate, monomer; available from BASF |
| PEGA | Poly(ethylene glycol) acrylate, monomer; available from Sigma-Aldrich (St. Louis, MO) |
| HEMA | 2-Hydroxyethyl methacrylate, monomer; available from Sigma-Aldrich (St. Louis, MO) |
| IOTG | Isooctyl thioglycolate, chain transfer agent; available from Sigma-Aldrich (St. Louis, MO) |
| ABP | 4-Acryloyloxy benzophenone, photo crosslinker; obtained from 3M Co. St Paul, MN) |
| PI | 2-Hydroxy-2-methyl-1-phenyl-propan-1-one, photoinitiator; available as "DAROCURE" 1173 from BASF (Florham Park, NJ) |
| AO | Octadecyl-3-(3,5-di-tert.-butyl-4-hydroxyphenyl)-propionate, antioxidant; available as "IRGANOX 1076" from BASF (Florham Park, NJ) |
| DURAPORE Tape | Medical tape with acrylic adhesive on silk backing, available from 3M (St. Paul, MN) |
| MULTIPORE Tape | Medical tape with acrylic adhesive on elastic fabric backing, available from 3M (St. Paul, MN) |
| KENDALL CAT | Medical Tape with rubber based adhesive on cloth backing, available from Cardinal Health (Dublin, OH) |

Test Methods

Gel Permeation Chromatography (GPC)

Number average molecular weights ($M_n$) and weight average molecular weights (Mw) were obtained by conventional gel permeation chromatography with light scattering detector using tetrahydrofuran as solvent and mobile phase. The equipment consisted of an Agilent 1100 system (pump, degasser, autosampler, column oven, differential refractive index detector) (Agilent Technologies, Santa Clara, CA, USA) operating at 40° C. and flow rate of 1.0 mL/min. The stationary phase consisted of a Jordi Gel DVB mixed column (250 mm×10 mm ID) (Jordi Labs, Mansfield, MA, USA). Molecular weight calculations were performed using Cirrus GPC software from Polymer Labs (now Agilent Technologies, Santa Clara, CA, USA).

Dynamic Mechanical Analysis (DMA)

DMA was used to measure the storage modulus, viscosity, and glass transition temperature of pre-adhesive compositions. A small sample of pre-adhesive composition was transferred onto the bottom plate of a rheometer (obtained from TA Instruments, New Castle, DE, under the trade designation "ARES G2 Rheometer"). The rheometer had 8 mm diameter parallel top and bottom plates. The top plate of the rheometer was brought onto the sample of pre-adhesive composition until the parallel plates were separated by 1 mm. A temperature sweep test method was used where shear moduli, viscosity, and tan($\delta$) were estimated while the sample was subjected to oscillatory shear (strain amplitude=1%, frequency=1 Hz) and at the same time the sample temperature was continuously increased from −65° C. to 175° C. at a rate of 5° C./min. Storage modulus (G') was reported in Pa. Tan ($\delta$) was calculated as the ratio G"/G' (loss modulus/storage modulus). The temperature, where the tan ($\delta$) curve had a local peak, was reported as the glass transition temperature ("$T_g$").

Percent Gel

Percent gel (gel content) was determined in generally similar manner as described in ASTM D3616-95 (as specified in 2009) with the following modifications: a test specimen measuring 63/64 inch in diameter was placed in a mesh basket measuring 1.5 in by 1.5 in. The basket with the specimen was weighed to the nearest 0.1 mg and placed in a capped jar containing sufficient amount of EtOAc to cover the sample. After 24 hours the basket (containing the specimen) was removed, drained and placed in an oven at 120° C. for 30 minutes. The percent gel was determined by rationing the weight of the remaining unextracted portion of the adhesive sample to the weight of the adhesive sample before extraction (to correct for the weight of the tape backing, a disc of the uncoated backing material of the same size as the specimen was die-cut and weighed). The formula used for percent gel determination was as shown below:

$$\text{Percent Gel (wt \%)} = 100 \times \frac{(\text{unextracted sample wt after extraction} - \text{backing wt})}{(\text{original sample wt} - \text{backing wt})}$$

Residual Monomer Analysis

Residual monomer content on the final pressure-sensitive adhesive composition was determined by gas chromatography according to the following procedure: A predetermined amount of sample was weighed in a dram vial and methanol was added. The vial was capped and shaken for 2 hours. A portion from the sample was transferred to an autosampler vial and was analyzed by a HP 6890 GCFID instrument. Column type J & W DB-5MS 30 m×0.25 mm×0.1 um, gas phase was He 2.0 ml/min. Standards were prepared by weighing known amounts of each sample, which were then analyzed to build a calibration range of ~0.05-1,000 µg/mL.

Peel Adhesion Test

Peel adhesion was measured at a 180° angle using a Zwick testing machine (available from Zwick, GA) at a peel rate of 12 inches/minute. Stainless steel test panels were prepared by wiping the substrate panels with a laboratory wipe wetted with 50% N-Heptane/50% Isopropanol using hand pressure to wipe three times. Adhesive tape samples were cut into stripes measuring ½ inch by 8 inches and the strips were rolled down onto the cleaned panel using a mechanical roller machine (preferred) or hand operated 4.5 lb. roller (no additional force necessary), roll once in each direction at a rate of approximately 2 in (50 mm)/second or mechanical roller machine set to 120 in/min. The prepared samples were stored at 25° C. and 50% relative humidity for the desired "dwell" time before testing. Peel strengths strength were reported as average values of 3 to 5 repeated experiments.

PVC panels were washed three times with heptane and then the same procedure was followed as in the case of stainless steel panels.

Soak test sample testing was performed using the peel adhesion test described above except the tape samples were soaked in a 3 mM of $CaCl_2$ aqueous solution (333 mg of $CaCl_2$ in 1 liter deionized water) for specified time (20 min or 60 min) prior to be applied onto SS testing panel.

Preparation of Pre-Adhesive Compositions and (meth)acrylate-Based Polymers

The pre-adhesive formulations were prepared following the methods described in U.S. Pat. No. 5,804,610 and cured to form (meth)acrylate-based polymers. The water bath temperature was 60° F., the UV intensity was 4.55 mW/cm² and the residence time was 17 minutes. The compositions for each formulation are listed in Table 1.

TABLE 1

| Sample | 2EHA | IOA | BA | 2-PHA | PI | AO | ABP | IOTG | HEA | HPA | PEGA | HEMA | HDDA |
|---|---|---|---|---|---|---|---|---|---|---|---|---|---|
| PRE-1 | 100 | — | — | — | 0.3 | — | 0.1 | 0.02 | — | — | — | — | — |
| PRE-2 | — | 96 | — | — | 0.3 | — | 0.1 | 0.04 | 4 | — | — | — | — |
| PRE-3 | — | 92 | — | — | 0.3 | — | 0.1 | 0.04 | — | 8 | — | — | — |
| PRE-4 | — | 96 | — | — | 0.3 | — | 0.1 | 0.06 | — | 4 | — | — | — |
| PRE-5 | — | 94 | — | — | 0.3 | — | 0.1 | 0.06 | — | 6 | — | — | — |
| PRE-6 | — | 92 | — | — | 0.3 | — | 0.1 | 0.06 | — | 8 | — | — | — |
| PRE-7 | — | 92 | — | — | 0.3 | — | 0.1 | 0.06 | — | 8 | — | — | — |
| PRE-8 | — | 90 | — | — | 0.3 | — | 0.1 | 0.06 | — | 10 | — | — | — |
| PRE-9 | 80 | — | — | — | 0.3 | — | 0.1 | 0.06 | — | 20 | — | — | — |
| PRE-10 | 70 | — | — | — | 0.3 | — | 0.1 | 0.06 | — | 30 | — | — | — |
| PRE-11 | — | 98 | — | — | 0.3 | 0.2 | 0.1 | 0.06 | — | 2 | — | — | — |
| PRE-12 | — | 90 | — | — | 0.3 | 0.2 | 0.1 | 0.06 | — | 10 | — | — | — |
| PRE-13 | — | 88 | — | — | 0.3 | 0.2 | 0.1 | 0.06 | — | 12 | — | — | — |
| PRE-14 | — | 86 | — | — | 0.3 | 0.2 | 0.1 | 0.06 | — | 14 | — | — | — |
| PRE-15 | — | 84 | — | — | 0.3 | 0.2 | 0.1 | 0.06 | — | 16 | — | — | — |
| PRE-16 | — | 82 | — | — | 0.3 | 0.2 | 0.1 | 0.06 | — | 18 | — | — | — |
| PRE-17 | — | 80 | — | — | 0.3 | 0.2 | 0.1 | 0.06 | — | 20 | — | — | — |
| PRE-18 | — | 70 | — | — | 0.3 | 0.2 | 0.1 | 0.06 | — | 30 | — | — | — |
| PRE-19 | — | — | 90 | — | 0.3 | 0.2 | 0.1 | 0.06 | — | 10 | — | — | — |
| PRE-20 | — | — | — | 90 | 0.3 | 0.2 | 0.1 | 0.06 | — | 10 | — | — | — |
| PRE-21 | — | 100 | — | — | 0.3 | 0.2 | 0.1 | 0.06 | — | — | — | — | — |
| PRE-22 | — | 92 | — | — | 0.3 | 0.2 | 0.1 | 0.08 | 8 | — | — | — | — |

TABLE 1-continued

| Sample | 2EHA | IOA | BA | 2-PHA | PI | AO | ABP | IOTG | HEA | HPA | PEGA | HEMA | HDDA |
|---|---|---|---|---|---|---|---|---|---|---|---|---|---|
| PRE-23 | — | 92 | — | — | 0.3 | 0.2 | 0.1 | 0.02 | 4 | — | 4 | — | — |
| PRE-24 | — | 92 | — | — | 0.3 | 0.2 | 0.1 | 0.02 | — | — | — | 8 | — |
| PRE-25 | — | 84 | — | — | 0.3 | 0.2 | 0.1 | 0.02 | 16 | — | — | — | — |
| PRE-26 | — | 90 | — | — | 0.3 | — | 0.05 | 0.06 | — | 10 | — | — | — |
| PRE-27 | 90 | — | — | — | 0.3 | — | 0.05 | 0.06 | — | 10 | — | — | — |
| PRE-28 | 90 | — | — | — | 0.3 | — | 0.05 | 0.1 | — | 10 | — | — | 0.06 |
| PRE-29 | 80 | — | — | — | 0.3 | — | 0.05 | 0.1 | — | 20 | — | — | 0.06 |
| PRE-30 | 90 | — | — | — | 0.3 | — | 0.05 | 0.16 | — | 10 | — | — | 0.09 |

Properties for the (meth)acrylate-based polymers were measured according to the test methods above. Test results are summarized in Table 2.

TABLE 2

| Sample | $M_n$ (g/mol) | $M_w$ (g/mol) | D ($M_w/M_n$) | $T_g$ (° C.) | G'(135° C., Pa) |
|---|---|---|---|---|---|
| PRE-1 | 107,000 | 918,000 | 8.58 | −57.6 | 1,258 |
| PRE-2 | 138,000 | 1,150,000 | 8.35 | −52.8 | 466 |
| PRE-3 | 123,000 | 832,000 | 6.79 | −43.4 | 203 |
| PRE-4 | 65,400 | 512,000 | 7.83 | −47.8 | 24 |
| PRE-5 | 123,000 | 662,000 | 5.41 | −45.3 | 68 |
| PRE-6 | 124,000 | 744,000 | 6.00 | −40.4 | 350 |
| PRE-7 | 104,000 | 741,000 | 7.13 | −43.3 | 190 |
| PRE-8 | 135,000 | 670,000 | 4.96 | −43.7 | 77 |
| PRE-9 | NT | NT | NT | NT | NT |
| PRE-10 | NT | NT | NT | NT | NT |
| PRE-11 | NT | NT | NT | −49.4 | NT |
| PRE-12 | NT | NT | NT | −55.2 | NT |
| PRE-13 | NT | NT | NT | −56.7 | NT |
| PRE-14 | NT | NT | NT | −41.5 | NT |

NT—Not Tested

UV Radiation Crosslinking

The (meth)acrylate-based polymers were fed to a twin screw extruder (Haake) with barrel temperatures set at 275° F. The pressure-sensitive adhesive was extruded to a thickness of 0.0254 mm onto a paper Web that was treated on both sides with a silicone release coating. The coated adhesive was then exposed to a medium pressure mercury vapor lamp having an output of about 80 Watts per cm and a spectral output over a range of 180 to 430 nm to provide a total energy of 50 mJ/cm². The pressure-sensitive adhesives PRE1-PRE21 and PRE27 were then laminated to an ESTANE 58237 thermoplastic polyurethane film commercially available from the Lubrizol Corporation and tested according to the above described test procedures for peel adhesion. Test results are shown in Table 3.

The pressure-sensitive adhesives PRE-22-PRE-25 and PRE27-PRE30 were extruded to a thickness of 0.072 mm onto a cellulose acetate backing, which was treated on the opposite side with a low adhesion coating. Test results are shown in Table 4. In addition, Example 13 had a gel fraction of 81% as determined using the percent gel method described herein.

TABLE 3

| Example | Pre-adhesive | % IOA | % EHA | % BA | % PHA | % HPA | % HEA | % ABP | % IOTG | Backing | Peel adhesion to PVC 20 min Dwell Time (oz/in) | Peel adhesion to PVC 24 h Dwell Time (oz/in) | Peel adhesion to SS 20 min Dwell Time (oz/in) | Peel adhesion to SS 24 h Dwell Time (oz/in) |
|---|---|---|---|---|---|---|---|---|---|---|---|---|---|---|
| CE1 | PRE-1 | — | 100 | — | — | 0 | — | | 0.02 | Polyurethane film | 4.8 | 9 | 4.8 | 4.8 |
| 1 | PRE-2 | 96 | — | — | — | — | 2 | | 0.04 | Polyurethane film | 11.9 | 22.1 | 8.2 | 8.2 |
| 2 | PRE-3 | 92 | — | — | — | 8 | — | | 0.04 | Polyurethane film | 28.2 | 26.1 | 15.9 | 24.3 |
| 3 | PRE-4 | 96 | — | — | — | 4 | — | | 0.06 | Polyurethane film | 25.2 | 24.6 | 13.9 | 22.5 |
| 4 | PRE-5 | 94 | — | — | — | 6 | — | | 0.06 | Polyurethane film | 27.2 | 27.5 | 16.7 | 23 |
| 5 | PRE-6 | 92 | — | — | — | 8 | — | | 0.06 | Polyurethane film | 26.5 | 17.2 | 23.4 | 30.8 |
| 6 | PRE-7 | 92 | — | — | — | 8 | — | | 0.06 | Polyurethane film | 24.5 | 18.9 | 10.7 | 18.9 |
| 7 | PRE-8 | 90 | — | — | — | 10 | — | | 0.06 | Polyurethane film | 33 | 18 | 18.7 | 34.7 |
| 8 | PRE-9 | — | 80 | — | — | 20 | — | | 0.06 | Polyurethane film | 12.7 | 11.4 | 9.6 | 18.9 |
| 9 | PRE-10 | — | 70 | — | — | 30 | — | 0.1 | 0.06 | Polyurethane film | 13.2 | 8.7 | 11.3 | 21.4 |
| 10 | PRE-11 | 98 | — | — | — | 2 | — | 0.1 | 0.06 | Polyurethane film | 20.1 | 23.9 | 12.3 | 25 |

TABLE 3-continued

| Example | Pre-adhesive | % IOA | % EHA | % BA | % PHA | % HPA | % HEA | % ABP | % IOTG | Backing | Peel adhesion to PVC 20 min Dwell Time (oz/in) | Peel adhesion to PVC 24 h Dwell Time (oz/in) | Peel adhesion to SS 20 min Dwell Time (oz/in) | Peel adhesion to SS 24 h Dwell Time (oz/in) |
|---|---|---|---|---|---|---|---|---|---|---|---|---|---|---|
| 11 | PRE-12 | 90 | — | — | — | 10 | — | 0.1 | 0.06 | Polyurethane film | 19.6 | 25.2 | 21 | 42.8 |
| 12 | PRE-13 | 88 | — | — | — | 12 | — | 0.1 | 0.06 | Polyurethane film | 20.9 | 24.3 | 21.6 | 50.8 |
| 13 | PRE-14 | 86 | — | — | — | 14 | — | 0.1 | 0.06 | Polyurethane film | 17.5 | 18.2 | 21.1 | 38.4 |
| 14 | PRE-15 | 84 | — | — | — | 16 | — | 0.1 | 0.06 | Polyurethane film | 19.1 | 18.1 | 22.7 | 30.9 |
| 15 | PRE-16 | 82 | — | — | — | 18 | — | 0.1 | 0.06 | Polyurethane film | 20.8 | 17.6 | 24.1 | 43 |
| 16 | PRE-17 | 80 | — | — | — | 20 | — | 0.1 | 0.06 | Polyurethane film | 24.9 | 19 | 21.5 | 30.2 |
| 17 | PRE-18 | 70 | — | — | — | 30 | — | 0.1 | 0.06 | Polyurethane film | 21.2 | 25.2 | 26.6 | 33 |
| 18 | PRE-19 | — | — | 90 | — | 10 | — | 0.1 | 0.06 | Polyurethane film | 22.5 | 19.7 | 12.4 | 27.1 |
| 19 | PRE-20 | — | — | — | 90 | 10 | — | 0.1 | 0.06 | Polyurethane film | 22.7 | 14.2 | 14.8 | 10.2 |
| 20 | PRE-21 | 100 | — | — | — | 0 | — | 0.1 | 0.06 | Polyurethane film | 14.9 | 22.9 | 15 | 21.6 |
| 21 | PRE-27 | — | 90 | — | — | 10 | — | 0.05 | 0.06 | Polyurethane film | 24.62 | 21.84 | 19.5 | 25.13 |

TABLE 4

| Ex. | Pre-adhesive | % 2EHA | % IOA | % HEA | % HPA | % PEGA | % HEMA | % HDDA | % ABP | % IOTG | Backing | Peel adhesion to PVC 20 min Dwell Time (oz/in) | Peel adhesion to PVC 24 h Dwell Time (oz/in) | Peel adhesion to SS 20 min Dwell Time (oz/in) | Peel adhesion to SS 24 h Dwell Time (oz/in) | 20 min Dwell after 20 min in soak solution (oz/in) | 21 min Dwell after 60 min in soak solution (oz/in) |
|---|---|---|---|---|---|---|---|---|---|---|---|---|---|---|---|---|---|
| CE 2 | Durapore Tape | | | | | | | | | | Cellulose acetate | 21.35 | NT | 13.22 | NT | 5.53 | 0 |
| CE 3 | Multipore Tape | | | | | | | | | | Fabric | 21.68 | NT | 25.17 | NT | 2.7 | 0 |
| CE 4 | Kendall Cloth Adhesive Tape | | | | | | | | | | Cloth | NT | NT | 33.61 | NT | 13.1 | 4.55 |
| 22 | PRE-22 | — | 92 | 8 | — | — | — | — | 0.1 | 0.08 | Cellulose acetate | 35.1 | 36.8 | 16.8 | 23.6 | NT | NT |
| 23 | PRE-23 | — | 92 | 4 | — | 5 | — | — | 0.1 | 0.02 | Cellulose acetate | 17.1 | 19.3 | 12.7 | 15.6 | NT | NT |
| 24 | PRE-24 | — | 92 | — | — | — | 8 | — | 0.1 | 0.02 | Cellulose acetate | 16.1 | 32 | 17 | 30.9 | NT | NT |
| 25 | PRE-25 | — | 84 | 16 | — | — | — | — | 0.1 | 0.02 | Cellulose acetate | 16..3 | 13.9 | 12 | 20.5 | NT | NT |
| 25 | PRE-27 | — | 90 | — | 10 | — | — | — | 0.05 | 0.06 | Cellulose acetate | 31.94 | 40.08 | 45.68 | 54.75 | NT | NT |
| 27 | PRE-28 | — | 90 | — | 10 | — | — | 0.06 | 0.05 | 0.1 | Cellulose acetate | 47.74 | NT | 60.42 | NT | 31.16 | 7.44 |
| 28 | PRE-29 | — | 80 | — | 20 | — | — | 0.06 | 0.05 | 0.1 | Cellulose acetate | 38.75 | NT | 46.58 | NT | 20.07 | 2.63 |

TABLE 4-continued

| Ex. | Pre-adhesive | % 2EHA | % IOA | % HEA | % HPA | % PEGA | % HEMA | % HDDA | % ABP | % IOTG | Backing | Peel adhesion to PVC 20 min Dwell Time (oz/in) | Peel adhesion to PVC 24 h Dwell Time (oz/in) | Peel adhesion to SS 20 min Dwell Time (oz/in) | Peel adhesion to SS 24 h Dwell Time (oz/in) | Peel adhesion to SS 20 min Dwell after 20 in min soak solution (oz/in) | Peel adhesion to SS 21 min Dwell after 60 in min soak solution (oz/in) |
|---|---|---|---|---|---|---|---|---|---|---|---|---|---|---|---|---|---|
| 29 | PRE-30 | 90 | — | — | 10 | — | — | 0.09 | 0.05 | 0.16 | Cellulose acetate | 49.36 | NT | 54.73 | NT | 27.2 | 3.17 |

Residual monomer analysis for each pressure-sensitive adhesive composition is summarized in Table 5. Residual monomer concentrations of no greater than 500 ppm suggest that Examples 1-9 and CE1 are suitable for skin adhesion applications.

TABLE 5

| Example | Residual IOA in ppm (** denotes HEA) | Residual HPA in ppm (* denotes EHA) |
|---|---|---|
| CE1 | 139 | — |
| 1 | 403 | <14 ** |
| 2 | 185 | 18 |
| 3 | 245 | 19 |
| 4 | 51 | <9 |
| 5 | 28 | 20 |
| 6 | 258 | 19 |
| 7 | 224 | 21 |
| 8 | <100 | <200 |
| 9 | <100 | <200 |

What is claimed is:

1. An article, comprising:
   a substrate; and
   a hot melt processable pressure sensitive adhesive disposed on at least a portion of the substrate, wherein the hot melt processable pressure sensitive adhesive does not comprise a tackifier, and wherein the hot melt processable pressure sensitive adhesive comprises a (meth)acrylate-based copolymer that is the reaction product of a reaction mixture that is free of acidic or basic monomers and comprises, as the polymerizable components:
   70-96 parts by weight of a first (meth)acrylate monomer of general formula I:

$$CH_2=CR^1—(CO)—OR^2 \quad \text{Formula I}$$

wherein $R^1$ is hydrogen or a methyl group; and
   $R^2$ is an alkyl, heteroalkyl, alkenyl, or aryl group;
   4-30 parts by weight of a second (meth)acrylate monomer of general formula II:

$$CH_2=CR^1—(CO)—OR^3 \quad \text{Formula II}$$

wherein $R^1$ is hydrogen or a methyl group; and
   $R^3$ is a hydroxyl substituted alkyl group, a hydroxyl substituted heterocyclic group, a hydroxyl substituted aryl group, or a hydroxyl substituted macromolecule; and
   a co-polymerizable photocrosslinker.

2. The article of claim 1, wherein the hot melt processable pressure sensitive adhesive further comprises particles of a thermoplastic polymer selected from the group consisting of polyethylene, ethylene vinyl acetate, ethylene methyl acrylate, ethylene acrylic acid, ethylene acrylic acid ionomers, polypropylene, acrylic polymers, polyphenylene ether, polyphenylene sulfide, acrylonitrile-butadiene-styrene copolymers, polyurethanes, and mixtures and blends thereof.

3. The article of claim 1, wherein the substrate is selected from the group consisting of a polymeric film, a fabric, a non-woven, a foam, a paper, a mesh, an adhesive, and a release liner.

4. The article of claim 1, wherein the reaction mixture comprises 80-96 parts by weight of the first (meth)acrylate monomer, and 4-20 parts by weight of the second (meth)acrylate monomer.

5. The article of claim 1, wherein the reaction mixture comprises 90-96 parts by weight of the first (meth)acrylate monomer, and 4-10 parts by weight of the second (meth)acrylate monomer.

6. The article of claim 1, wherein the (meth)acrylate-based copolymer has a glass transition temperature of −20° C. or lower.

7. The article of claim 1, wherein the (meth)acrylate-based copolymer has a weight average molecular weight Mw of 500,000 grams/mole or greater.

8. The article of claim 1, wherein the first monomer has a homopolymer glass transition temperature of −20° C. or lower.

9. The article of claim 1, wherein the $R^2$ of the first (meth)acrylate monomer is an alkyl group having 1 to 14 carbon atoms.

10. The article of claim 1, wherein the $R^3$ of the second (meth)acrylate monomer comprises:
    a hydroxyl-substituted alkyl group comprising 2-6 carbon atoms; or
    a macromolecular group comprising a hydroxyl-terminated alkylene-oxide group,
    wherein the alkylene-oxide group comprises repeat units of the formula —($R^4$—O-)n-, where $R^4$ is an alkyl group containing 2-4 carbon atoms, and n is an integer from 3-100.

11. The article of claim 1, wherein the hot melt processable pressure sensitive adhesive has been photocrosslinked.

12. A packaged adhesive composition, comprising:
    a hot melt processable adhesive comprising a polymerized (meth)acrylate-based copolymer formed from a polymerizable pre-adhesive mixture, wherein the hot melt processable pressure sensitive adhesive does not comprise a tackifier, and wherein the polymerizable pre-adhesive mixture composition is free of acidic or basic monomers and comprises:
    70-96 parts by weight of a first (meth)acrylate monomer of general formula I:

$$CH_2=CR^1—(CO)—OR^2 \quad \text{Formula I}$$

wherein $R^1$ is hydrogen or a methyl group; and
$R^2$ is an alkyl, heteroalkyl, alkenyl, or aryl group;
4-30 parts by weight of a second (meth)acrylate monomer of general Formula II:

$$CH_2=CR^1-(CO)-OR^3 \quad \text{Formula II}$$

wherein $R^1$ is hydrogen or a methyl group; and
$R^3$ is a hydroxyl substituted alkyl group, a hydroxyl substituted heterocyclic group, a hydroxyl substituted aryl group, or a hydroxyl substituted macromolecule;
a co-polymerizable photocrosslinker; and
at least one initiator; and
a packaging material.

13. The packaged adhesive composition of claim 12, wherein the polymerizable pre-adhesive mixture composition further comprises a chain transfer agent.

14. The packaged adhesive composition of claim 12, wherein the polymerizable pre-adhesive mixture composition comprises 80-96 parts by weight of the first (meth)acrylate monomer, and 4-20 parts by weight of the second (meth)acrylate monomer.

15. The packaged adhesive composition of claim 12, wherein the polymerizable pre-adhesive mixture composition comprises 90-96 parts by weight of the first (meth)acrylate monomer, and 4-10 parts by weight of the second (meth)acrylate monomer.

16. The packaged adhesive composition of claim 12, wherein the polymerized (meth)acrylate-based copolymer has a weight average molecular weight Mw of 500,000 grams/mole or greater.

17. The packaged adhesive composition of claim 12, wherein the packaging material comprises a thermoplastic polymer selected from the group consisting of polyethylene, ethylene vinyl acetate, ethylene methyl acrylate, ethylene acrylic acid, ethylene acrylic acid ionomers, polypropylene, acrylic polymers, polyphenylene ether, polyphenylene sulfide, acrylonitrile-butadiene-styrene copolymers, polyurethanes, and mixtures and blends thereof.

18. A method of preparing an adhesive article, the method comprising:
providing a substrate with a first major surface and a second major surface;
providing a hot melt processable packaged adhesive composition that:
a hot melt processable adhesive that does not comprise a tackifier, wherein the hot melt processable adhesive comprises a polymerized (meth)acrylate-based copolymer formed from a polymerizable pre-adhesive mixture, wherein the polymerizable pre-adhesive mixture composition is free of acidic or basic monomers and comprises:
70-96 parts by weight of a first (meth)acrylate monomer of general Formula I:

$$CH_2=CR^1-(CO)-OR^2 \quad \text{Formula I}$$

wherein $R^1$ is hydrogen or a methyl group; and
$R^2$ is an alkyl, heteroalkyl, alkenyl, or aryl group; and
4-30 parts by weight of a second (meth)acrylate monomer of general Formula II:

$$CH_2=CR^1-(CO)-OR^3 \quad \text{Formula II}$$

wherein $R^1$ is hydrogen or a methyl group; and
$R^3$ is a hydroxyl substituted alkyl group, a hydroxyl substituted heterocyclic group, a hydroxyl substituted aryl group, or a hydroxyl substituted macromolecule;
a co-polymerizable photocrosslinker; and
at least one initiator; and
a packaging material;
hot melt processing the packaged adhesive composition;
disposing the hot melt processed packaged adhesive composition on at least a portion of the second major surface of the substrate to form a pressure sensitive adhesive layer; and
photocrosslinking the pressure sensitive adhesive layer.

19. The method of claim 18, wherein the packaging material is selected from the group consisting of polyethylene, ethylene vinyl acetate, ethylene methyl acrylate, ethylene acrylic acid, ethylene acrylic acid ionomers, polypropylene, acrylic polymers, polyphenylene ether, polyphenylene sulfide, acrylonitrile-butadiene-styrene copolymers, polyurethanes, and mixtures and blends thereof.

20. The method of claim 18, wherein the polymerizable pre-adhesive mixture further comprises a chain transfer agent.

\* \* \* \* \*